United States Patent
Burke et al.

(10) Patent No.: US 10,463,754 B2
(45) Date of Patent: Nov. 5, 2019

(54) PROCESS FOR DECONTAMINATING OR STERILIZING AN ARTICLE

(71) Applicant: American Sterilizer Company, Mentor, OH (US)

(72) Inventors: Peter A. Burke, Concord, OH (US); Mark James Leggett, Cardiff (GB); Michael A. Centanni, Parma, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 14/537,958

(22) Filed: Nov. 11, 2014

(65) Prior Publication Data

US 2015/0306266 A1    Oct. 29, 2015

Related U.S. Application Data

(63) Continuation-in-part of application No. 14/525,497, filed on Oct. 28, 2014, which is a continuation-in-part of application No. 14/262,840, filed on Apr. 28, 2014.

(51) Int. Cl.
    *A61L 2/18*     (2006.01)
    *A01N 37/16*    (2006.01)
    *A01N 59/00*    (2006.01)

(52) U.S. Cl.
    CPC .............. *A61L 2/186* (2013.01); *A01N 37/16* (2013.01); *A01N 59/00* (2013.01)

(58) Field of Classification Search
    CPC ........... A61L 2/18; A61L 2/186; A01N 37/16; A01N 59/00; A61K 8/22
    See application file for complete search history.

(56) References Cited

U.S. PATENT DOCUMENTS

| | | | |
|---|---|---|---|
| 3,786,615 A |   | 1/1974 | Bauer |
| 4,051,058 A | * | 9/1977 | Bowing .................. A01N 37/16 252/186.22 |
| 4,051,059 A | * | 9/1977 | Bowing .................. A01N 37/16 252/186.23 |
| 4,235,332 A | * | 11/1980 | Andersen ........... B65D 81/3261 116/206 |
| 4,269,602 A |   | 5/1981 | Worth |

(Continued)

FOREIGN PATENT DOCUMENTS

| EP | 1252819 | 10/2002 |
|---|---|---|
| EP | 1293215 A1 | 3/2003 |

(Continued)

OTHER PUBLICATIONS

English translation of JP-06206825-A (Year: 1994).*

(Continued)

*Primary Examiner* — Regina M Yoo
(74) *Attorney, Agent, or Firm* — Renner, Otto, Boisselle & Sklar, LLP

(57) ABSTRACT

This invention relates to a a process for decontaminating or sterilizing an article contaminated with spores. The process comprises contacting the spores with a liquid sterilant for a sufficient period of time to effect a desired reduction (e.g., at least a 4 log reduction) in the number of spores capable of returning to vegetative growth. The liquid sterilant may comprise water, an antimicrobial agent (e.g., peracetic acid) and a peroxide (e.g., hydrogen peroxide).

9 Claims, 3 Drawing Sheets

(56) References Cited

U.S. PATENT DOCUMENTS

| | | | |
|---|---|---|---|
| 4,731,222 A | 3/1988 | Kralovic et al. | |
| 4,743,447 A | 5/1988 | Le Rouzic | |
| 4,892,706 A | 1/1990 | Kralovic et al. | |
| 4,896,768 A | 1/1990 | Anderson | |
| 4,910,014 A | 3/1990 | Nakagawa | |
| 5,190,724 A | 3/1993 | Hachmann | |
| 5,389,369 A * | 2/1995 | Allen | A01N 63/00 422/28 |
| 5,427,801 A * | 6/1995 | Uehara | A61K 8/19 424/613 |
| 5,437,868 A | 8/1995 | Oakes | |
| 5,472,715 A * | 12/1995 | Uehara | A61K 8/19 424/613 |
| 5,508,046 A | 4/1996 | Cosentino et al. | |
| 5,527,508 A | 6/1996 | Childers et al. | |
| 5,656,302 A | 8/1997 | Cosentino | |
| 5,767,163 A * | 6/1998 | Kundsin | A61K 31/045 514/557 |
| 5,770,232 A * | 6/1998 | Sizer | A01N 59/00 424/606 |
| 5,851,483 A * | 12/1998 | Nicolle | A01N 59/00 422/28 |
| 5,900,256 A | 5/1999 | Scoville, Jr. | |
| 6,103,189 A * | 8/2000 | Kralovic | A61L 2/186 134/22.1 |
| 6,168,808 B1 | 1/2001 | Golden et al. | |
| 6,187,555 B1 * | 2/2001 | Tautvydas | A61L 2/07 435/176 |
| 6,224,827 B1 | 5/2001 | Lembke | |
| 6,305,531 B1 | 10/2001 | Wilkman | |
| 6,326,032 B1 * | 12/2001 | Richter | A23G 9/30 252/186.23 |
| 6,346,279 B1 | 2/2002 | Rochon | |
| 6,448,062 B1 | 9/2002 | Huth | |
| 6,589,565 B1 | 7/2003 | Richter | |
| 6,686,324 B2 | 2/2004 | Ramirez et al. | |
| 6,734,405 B2 | 5/2004 | Centanni et al. | |
| 6,803,057 B2 | 10/2004 | Ramirez et al. | |
| 6,906,296 B2 | 6/2005 | Centanni et al. | |
| 6,967,315 B2 | 11/2005 | Centanni et al. | |
| 7,135,142 B2 | 11/2006 | Burke et al. | |
| 7,300,638 B2 | 11/2007 | Williams et al. | |
| 7,354,604 B2 | 4/2008 | Ramirez et al. | |
| 7,435,303 B2 | 10/2008 | Biering | |
| 7,569,182 B2 | 8/2009 | Burke et al. | |
| 7,632,523 B2 | 12/2009 | Ramirez et al. | |
| 7,655,252 B2 * | 2/2010 | Baker, Jr. | A61K 8/062 424/400 |
| 7,670,967 B2 * | 3/2010 | Runge | A61K 8/0208 442/102 |
| 7,781,388 B2 | 8/2010 | Heintz | |
| 8,143,309 B2 | 3/2012 | Awad | |
| 8,470,755 B1 * | 6/2013 | Tajmamet | A01N 59/16 510/235 |
| 2001/0001479 A1 | 5/2001 | Johnson | |
| 2003/0086820 A1 * | 5/2003 | McDonnell | A61K 31/327 422/28 |
| 2003/0096720 A1 | 5/2003 | Huth et al. | |
| 2003/0099717 A1 | 5/2003 | Cabrera | |
| 2003/0180377 A1 | 9/2003 | Ramirez et al. | |
| 2004/0022867 A1 | 2/2004 | Tucker et al. | |
| 2004/0047915 A1 | 3/2004 | Day | |
| 2005/0084415 A1 | 4/2005 | McVey et al. | |
| 2005/0095168 A1 | 5/2005 | Centanni et al. | |
| 2005/0238732 A1 * | 10/2005 | Lu | A01N 25/22 424/717 |
| 2005/0260107 A1 * | 11/2005 | Jackson | A61L 2/14 422/136 |
| 2006/0003649 A1 * | 1/2006 | Runge | A61K 8/0208 442/59 |
| 2006/0204467 A1 * | 9/2006 | Littau | A01N 31/02 424/70.13 |
| 2006/0229225 A1 | 10/2006 | Martin et al. | |
| 2006/0292031 A1 | 12/2006 | Chiu | |
| 2007/0006551 A1 * | 1/2007 | Sizer | A61L 2/186 53/426 |
| 2007/0053850 A1 | 3/2007 | Tichy | |
| 2007/0149435 A1 * | 6/2007 | Koenig | A61K 8/0208 510/384 |
| 2007/0264356 A1 * | 11/2007 | Ames | A61L 2/186 424/616 |
| 2008/0045593 A1 | 2/2008 | Kaiser et al. | |
| 2008/0178412 A1 * | 7/2008 | Kiter | A61L 2/10 15/309.2 |
| 2008/0240978 A1 * | 10/2008 | Sorensen | A61L 2/183 422/20 |
| 2009/0061017 A1 | 3/2009 | Pedersen et al. | |
| 2009/0074881 A1 | 3/2009 | Kielbania, Jr. | |
| 2009/0199360 A1 * | 8/2009 | Madanat | B62B 5/06 16/111.1 |
| 2009/0252775 A1 | 10/2009 | Arndt | |
| 2010/0106103 A1 * | 4/2010 | Ziebol | A61L 2/186 604/265 |
| 2010/0189599 A1 | 7/2010 | Bobbert | |
| 2010/0234828 A1 * | 9/2010 | Boyle | A61K 31/04 604/506 |
| 2010/0284855 A1 | 11/2010 | Erickson | |
| 2011/0076192 A1 | 3/2011 | Robitaille et al. | |
| 2011/0217204 A1 * | 9/2011 | Franciskovich | A01N 37/16 422/29 |
| 2012/0107415 A1 * | 5/2012 | Lisowsky | A01N 43/08 424/615 |
| 2012/0171300 A1 | 7/2012 | Koenig et al. | |
| 2012/0174872 A1 | 7/2012 | Richards | |
| 2012/0189494 A1 | 7/2012 | Rovison, Jr. et al. | |
| 2012/0230870 A1 | 9/2012 | Franciskovich et al. | |
| 2013/0251590 A1 * | 9/2013 | Golden | A01N 59/00 422/24 |
| 2014/0004208 A1 | 1/2014 | Golden et al. | |
| 2014/0037499 A1 | 2/2014 | Shannon et al. | |
| 2015/0314025 A1 | 11/2015 | Berentsveig et al. | |
| 2016/0095592 A1 * | 4/2016 | Levinson | A61F 13/023 606/219 |

FOREIGN PATENT DOCUMENTS

| | | | | |
|---|---|---|---|---|
| JP | | 06206825 A | * 7/1994 | A61K 8/19 |
| JP | | 7-126109 | 5/1995 | |
| JP | | 2001199811 A1 | 7/2001 | |
| WO | | 8808667 | 11/1988 | |
| WO | | 2004020562 | 3/2004 | |
| WO | | 2008111893 | 9/2008 | |
| WO | WO | 2012075507 A2 | 6/2012 | |
| WO | WO | 2013037014 A1 | 3/2013 | |

OTHER PUBLICATIONS

International Search Report and Written Opinion, Application No. PCT/US2015/015091, dated Apr. 30, 2015.
U.S. Appl. No. 14/262,840, filed Apr. 28, 2014.
U.S. Appl. No. 14/525,497, filed Oct. 28, 2014.
U.S. Appl. No. 14/538,011, filed Nov. 11, 2014.
Khadre et al.; "Sporicidal action of ozone and hydrogen peroxide: a comparative study"; International Journal of Food Microbiology 71 (2001); pp. 131-138.
"Guideline for Disinfection and Sterilization in Healthcare Facilities, 2008"; Centers for Disease Control and Prevention; CDC—Disinfection & Sterilization Guideline: Disinfection—HICPAC; http://www.cdc.gov/hicpac/disinfection_sterilization/6; 6 pages, Nov. 2008.
STERIS® Product Brochure; SPOR-KLENZ® Ready to Use; Dec. 1, 2001; 3 pages.
Minntech Renal Systems; Actril® Cold Sterilant Product Brochure; Technical Notes and Research Data; Oct. 1, 1998; 12 pages.
Ecolab; Oxonia Active Product Brochure; 2003; 2 pages.
International Preliminary Report on Patentability, Application No. PCT/US2015/015087, dated Jul. 14, 2016.
International Preliminary Report on Patentability, Application No. PCT/US2015/015088, dated Jun. 30, 2016.

(56) References Cited

OTHER PUBLICATIONS

International Preliminary Report on Patentability, Application No. PCT/US2015/015090, dated Jul. 14, 2016.
International Preliminary Report on Patentability, Application No. PCT/US2015/015091, dated Jul. 14, 2016.
Written Opinion of the International Preliminary Examining Authority, Application No. PCT/US2015/015091, dated Mar. 31, 2016.
Alasri et al., Canadian Journal of Microgiology 1993 (39):52-60.
Burke; 410(k) Summary for System 1E Liquid Chemical Sterilant Processing System; STERIS Corporation; Summary Date; Apr. 1, 2010.

* cited by examiner

PROCESS FOR DECONTAMINATING OR STERILIZING AN ARTICLE

This is a continuation-in-part of U.S. application Ser. No. 14/262,840, filed Apr. 28, 2014. This application is also a continuation-in-part of U.S. application Ser. No. 14/525,497, filed Oct. 28, 2014. These prior applications are incorporated herein by reference.

TECHNICAL FIELD

This invention relates to a process for decontaminating or sterilizing an article contaminated with spores, using an aqueous composition containing an antimicrobial agent (e.g., peracetic acid) and a peroxide (e.g., hydrogen peroxide).

BACKGROUND

Spores are a highly resistant, dormant cell type formed by some types of bacteria. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore specific layers. The mother cell then disintegrates, releasing the mature dormant spore which requires neither nutrients, water nor air for survival and is protected against a variety of trauma, including extremes of temperature, radiation, and chemical assault. Spore forming bacteria cause a number of serious diseases in humans, including botulism, gas gangrene, tetanus, and acute food poisoning. Anthrax results from infection by the aerobic spore form *Bacillus anthracis*.

SUMMARY

Spores are difficult to kill and a problem in the art of decontamination and sterilization relates to providing an effective process for killing spores. This invention provides a solution to this problem. This invention relates to a decontamination or sterilization process wherein spores are killed using a liquid sterilant comprising water, an antimicrobial agent (e.g., peracetic acid) and a peroxide (e.g., hydrogen peroxide).

Medical, dental, pharmaceutical, veterinary or mortuary instruments and devices that are exposed to blood or other body fluids (e.g., endoscopes) require sterilizing or disinfecting between each use. Liquid sterilizing or disinfecting systems are used to clean and decontaminate instruments and devices that cannot withstand the high temperatures of steam sterilization.

This invention relates to a process for decontaminating or sterilizing an article contaminated with spores, comprising: contacting the article with a liquid sterilant comprising water, an antimicrobial agent and a peroxide for a sufficient period of time to effect at least a 4 log reduction, or at least a 5 log reduction, or at least a 6 log reduction in the number of spores capable of returning to vegetative growth, the aqueous composition having a concentration of peroxide in the range from about 0.01 to about 14% by weight, or from about 0.01 to about 12% by weight, or from about 0.01 to about 10% by weight, or from about 0.01 to about 8% by weight, or from about 0.01 to about 7% by weight, or from about 0.05 to about 7% by weight, or from about 0.1 to about 7% by weight, or from about 0.1 to about 6.5% by weight.

In an embodiment, the concentration of the antimicrobial agent is in the range from about 0.001 to about 95% by weight, or from about 0.001 to about 80%, or from about 0.001 to about 60% by weight, or from about 0.001 to about 30% by weight, or from about 0.001 to about 10% by weight, or from about 0.001 to about 7% by weight, or from about 0.001 to about 6%, or from about 0.001 to about 5% by weight, or from about 0.001 to about 4% by weight, or from about 0.001 to about 3% by weight, or from about 0.001 to about 2% by weight, or from about 0.001 to about 1% by weight, or from about 0.001 to about 0.5% by weight, or from about 0.001 to about 0.4% by weight, or from about 0.001 to about 0.3% by weight, or from about 0.001 to about 0.2% by weight, or from about 0.001 to about 0.16% by weight.

In an embodiment, the concentration of the antimicrobial agent is in the range from about 0.005 to about 0.5% by weight, or from about 0.005 to about 0.4% by weight, or from about 0.005 to about 0.3% by weight, or from about 0.005 to about 0.2% by weight, or from about 0.005 to about 0.16% by weight.

In an embodiment, the weight ratio of the antimicrobial agent to the peroxide is in the range from about 0.001 to about 0.5, or from about 0.003 to about 0.4, or from about 0.006 to about 0.3, or from about 0.008 to about 0.2, or from about 0.01 to about 0.1.

In an embodiment, the process is conducted in a sterilizing apparatus, the sterilizing apparatus comprising a sterilization chamber and a sterilant introduction system, the process comprising: placing an article contaminated with spores in the sterilization chamber; flowing the liquid sterilant in the sterilization chamber in contact with the article; draining the liquid sterilant from the sterilization chamber; flowing rinse water in the sterilization chamber in contact with the article; and removing the article from the sterilization chamber.

DETAILED DESCRIPTION

Figure 1:
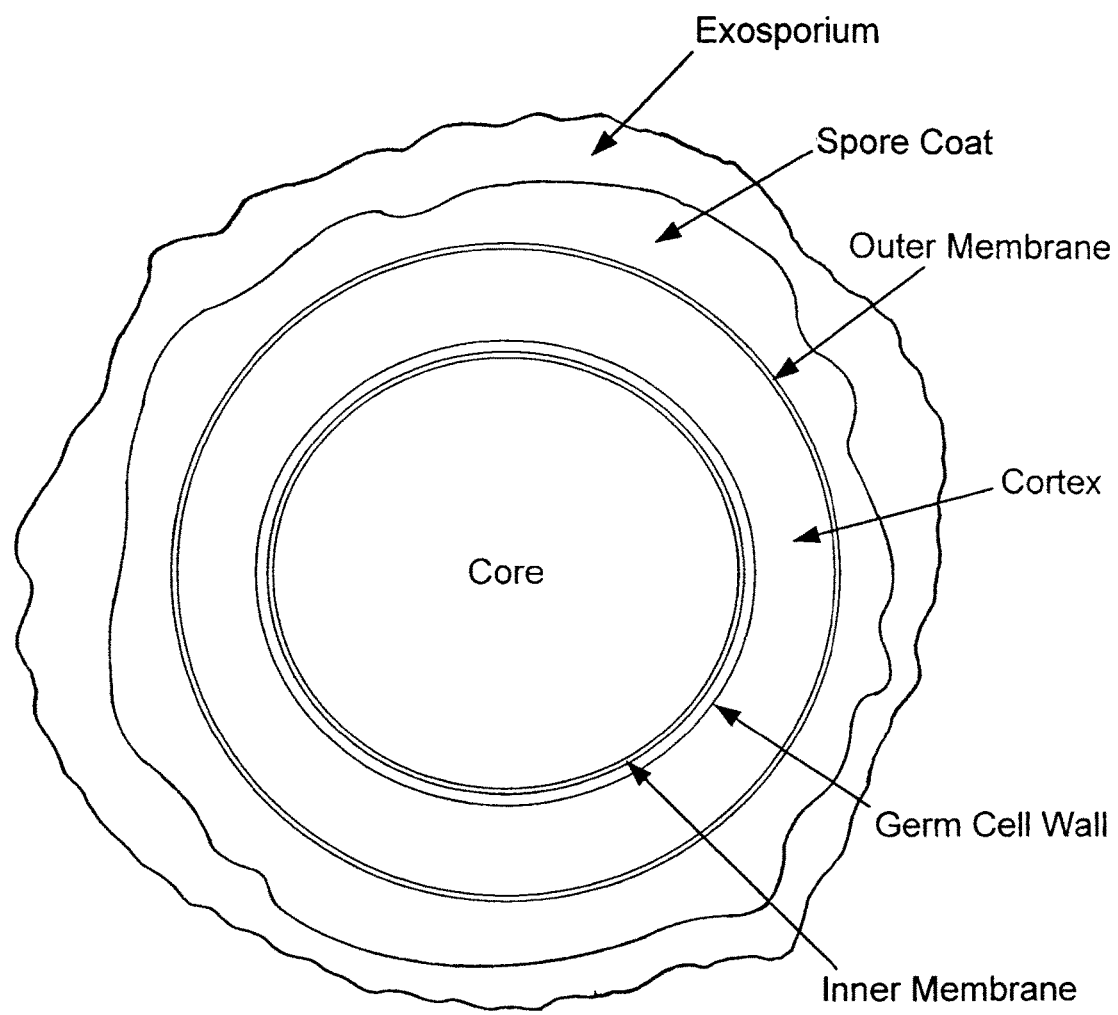
FIG. 1 is a schematic illustration of a bacterial spore that can be killed in accordance with the invention.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "killing" (or "kill") spores refers to rendering the spores incapable of returning to vegetative growth. In an embodiment, the term killing spores refers to rendering the spores incapable of reproduction, metabolism and/or growth.

The term "log reduction" is a mathematical term to show the number of live spores killed by contacting the spores with the aqueous composition of the invention. A "4 log reduction" means that the number of live spores is 10,000 times smaller. A "5 log reduction" means that the number of live spores is 100,000 times smaller. A "6 log reduction" means that the number of live spores is 1,000,000 times smaller.

The term "antimicrobial agent" refers to a substance that kills microorganisms or inhibits their growth.

The term "disinfectant" refers to a substance that is applied to non-living objects to kill or inhibit the growth of microorganisms that are on the objects.

The term "antibiotic" refers to a substance that kills or inhibits the growth of microorganisms within the body.

The term "antiseptic" refers to a substance that kills or inhibits the growth of microorganisms on living tissue.

The term "biocide" refers to a substance that kills or inhibits the growth of living organisms. The biocide can be a pesticide. The biocide can be a fungicide, herbicide, insecticide, algaecide, molluscicide, miticide or rodenticide.

The term "sanitizer" refers to a substance that cleans and disinfects.

Sterilization with respect to spores is often taken as referring to a process for achieving a total absence of living spores. Processes that are less rigorous than sterilization may include decontamination processes, and the like. The liquid sterilant provided for herein may be used to achieve at least a 4 log reduction, or at least a 5 log reduction, or at least a 6 log reduction in the number of spores capable of returning to vegetative growth, or in an embodiment, capable of reproduction, metabolism and/or growth. When at least a 6 log reduction is achieved, the process may be referred to as a sterilization process. When a 4 log reduction or a 5 log reduction is achieved, the process may be considered to be less rigorous than a sterilization, but nevertheless useful for various decontamination applications.

Bacterial spores typically comprise multiple concentric layers surrounding a central core. This is illustrated in FIG. 1 wherein a bacterial spore is shown which has a central core, inner membrane, germ cell wall, cortex, outer membrane, spore coat and occasionally an exosporium. Oxidizing agents for years have been thought to attack DNA, RNA, protein and most organic matter equally. However, while not wishing to be bound by theory, with the present invention it is believed that the mechanism that is provided involves the peroxide (e.g., hydrogen peroxide) first piercing holes in multiple layers surrounding the central core of the spores, and then the antimicrobial agent advancing through the pierced holes and attacking the central core to kill the spores. This mechanism is believed to occur when using liquid sterilant compositions with relatively low concentrations of the peroxide (e.g., in the range from about 0.01 to about 14% by weight, or from about 0.01 to about 7% by weight).

In embodiments wherein the concentrations of the antimicrobial agent and peroxide are relatively low, as indicated above, advantages of the inventive process include relatively low costs due to the fact that the concentrations of the antimicrobial agent and peroxide used in the processes are relatively low in comparison to normal concentrations used in other products using these ingredients. Other advantages of these embodiments include low levels of corrosion of surfaces treated due to the low concentrations of the antimicrobial agent and peroxide.

The water may comprise tap water, deionized water, distilled water, water purified by osmosis, or a mixture of two or more thereof.

The peroxide may comprise any compound containing an oxygen-oxygen single bond, or a peroxide group or peroxide ion. Examples include hydrogen peroxide; organic peroxides (e.g., benzoyl peroxide, acetyl acetone peroxide, acetyl benzoyl peroxide, diacetyl peroxide, methyl ethyl ketone peroxide, methyl isobutyl ketone peroxide, acetone peroxide, or a mixture of two or more thereof); peroxy acids (e.g., peroxy carboxylic acid); organic hydroperoxides (e.g., t-butyl hydroperoxide, ethylhydroperoxide, or cumene hydroperoxide); inorganic peroxides such as peroxide salts (e.g., alkali metal or alkaline earth metal peroxides); acid peroxides (e.g., peroxymonosulfuric acid or peroxydisulfuric acid); and mixtures of two or more thereof.

The hydrogen peroxide may be derived from any source of hydrogen peroxide. Hydrogen peroxide is typically available as a solution in water. Hydrogen peroxide concentrations of about 3 to about 8% by weight may be used. Commercial grades of about 30% to about 40% by weight, or about 35% by weight, hydrogen peroxide may be used. Commercial grades of about 70 to about 98% by weight hydrogen peroxide may be used. The higher concentrations would be diluted to provide the desired concentrations of hydrogen peroxide that are indicated above.

The antimicrobial agent may comprise a disinfectant, antibiotic, antiseptic, biocide and/or sanitizer. The antimicrobial agent may comprise peracetic acid. The antimicrobial agent may comprise an alcohol, chlorine, a chlorine compound, an aldehyde, an oxidizing agent, iodine, ozone, a phenolic, a quaternary ammonium compound, or a mixture of two or more thereof. The antimicrobial agent may comprise formaldehyde, ortho-phthalaldehyde, glutaraldehyde, silver dihydrogen citrate, polyaminopropyl biguanide, sodium bicarbonate, lactic acid, chlorine bleach, or a mixture of two or more thereof. The antimicrobial agent may comprise methanol, ethanol, n-propanol, 1-propanol, 2-propanol, isopropanol, or a mixture of two or more thereof. The antimicrobial agent may comprise a hypochlorite, chlorine dioxide, a dichloroisocyanurate, a monochloroisocyanurate, a halogenated hydantoin, or a mixture of two or more thereof. The antimicrobial agent may comprise sodium hypochlorite, calcium hypochlorite, sodium dichloroisocyanurate, sodium chlorite, N-chloro-4-methylbenzenesulfonamide sodium salt, 2,4-dichorobenzyl alcohol, or a mixture of two or more thereof. The antimicrobial agent may comprise performic acid, potassium permanganate, potassium peroxymonosulfate, or a mixture of two or more thereof. The antimicrobial agent may comprise phenol, o-phenylphenol, chloroxylenol, hexachlorophene, thymol, amylmetacresol, or a mixture of two or more thereof. The antimicrobial agent may comprise benzalkonuim chloride, cetyltrimethyl ammonium bromide, cetylpyridinium chloride, benzethonium chloride, boric acid, Brilliant green, chlorhexidine gluconate, tincture of iodine, providone-iodine, mercurochrome, manuka honey, octenidine dihydrochloride, polyhexamethylene biguamide, balsam of Peru, or a mixture of two or more thereof. Many of these antimicrobial agents may not be effective in the killing of spores on their own, but when combined with hydrogen peroxide at the concentration levels indicated above many of these antimicrobial agents are useful for killing spores.

The liquid sterilant composition may further comprise acetic acid, sulfuric acid, or a mixture thereof. The concentration of acetic acid may range up to about 60% by weight, or from about 0.001 to about 60% by weight, or from about 0.001 to about 30% by weight, or from about 0.001 to about 10% by weight, or from about 0.001 to about 5% by weight, or from about 0.001 to about 2% by weight. The concentration of sulfuric acid may range up to 3% by weight, or from about 0.001 to about 2% by weight. The concentration of each of these may be in the range up to about 1% by weight, or from about 0.001 to about 1% by weight, or from about 0.001 to about 0.5% by weight, or from about 0.001 to about 0.3% by weight.

The liquid sterilant composition may further comprise one or more surfactants to provide the aqueous composition with surface active properties, one or more buffers to provide buffering capability (pH modulation), one or more corrosion inhibitors to provide corrosion inhibiting properties, and/or one or more chelators to provide chelation capacity (water softening).

The surfactant may comprise any compound that lowers surface tension or provides greater wettability. The surfactant may comprise one or more detergent, wetting agents, emulsifiers, foaming agents and/or dispersants. The surfactant may comprise one or more organic compounds that contain both hydrophobic groups and hydrophilic groups. The surfactant may comprise both a water insoluble component and a water soluble component. The surfactant may comprise one or more anionic, cationic, zwitterionic and/or nonionic compounds. The surfactant may comprise one or more alkanolamines, alkylarylsulfonates, amine oxides, poly(oxyalkylene)s, block copolymers comprising alkylene oxide repeat units, carboxylated alcohol ethoxylates, ethoxylated alcohols, alkyl phenols, ethoxylated alkyl phenols, ethoxylated amines, ethoxylated amides, oxiranes, ethoxylated fatty acids, ethoxylated fatty esters, ethoxylated oils, fatty esters, fatty acid amides, glycerol esters, glycol esters, sorbitan, sorbitan esters, imidazolines, lecithin, lignin, glycerides (e.g., mono-, di- and/or triglyceride), olefin sulfonates, phosphate esters, ethoxylated and/or propoxylated fatty acids and/or alcohols, sucrose esters, sulfates and/or alcohols and/or ethoxylated alcohols of fatty esters, sulfonates of dodecyl and/or tridecyl benzenes, sulfosuccinates, dodecyl and/or tridecyl benzene sulfonic acids, mixtures of two or more thereof, and the like. The surfactant may comprise ethanolamine, triethanolamine, octyldimethylamine oxide, nonylphenoxy poly(ethyleneoxy)ethanol, polyalkylene glycol, or a mixture of two or more thereof. The concentration of the surfactant in the liquid sterilant composition may be in the range up to about 10% by weight, or from about 0.5 to about 10% by weight, or from about 0.5 to about 6% by weight, or from about 1 to about 4% by weight.

The buffer may comprise an alkali metal phosphate, an alkali metal carbonate, or a mixture thereof. The alkali metal may comprise sodium or potassium. The buffer may comprise one or more of monosodium phosphate, disodium phosphate, trisodium phosphate, monopotassium phosphate, dipotassium phosphate, tripotassium phosphate, sodium carbonate, or a mixture of two or more thereof. Disodium phosphate may be used. The concentration of the buffer in the liquid sterilant composition may be in the range up to about 50% by weight, or from about 1% by weight to about 50% by weight, or from about 1% by weight to about 40% by weight, or from about 5% by weight to about 40% by weight, or from about 5% by weight to about 35% by weight.

The corrosion inhibitor may comprise benzotriazole, a sodium salt of benzotriazole, tolyltriazole, a sodium salt of tolyltriazole, or a mixture of two or more thereof. Sodium benzotriazole may be used. A commercially available sodium benzotriazole that may be used is available under the trade designation Cobratec 40S which is believed to be a 40% by weight aqueous solution of sodium benzotriazole. The concentration of the corrosion inhibitor in the liquid sterilant composition may be in the range up to about 10% by weight, or from about 0.01% by weight to about 10% by weight, or from about 0.01% by weight to about 5% by weight.

The chelator may comprise ethylenediaminetetraacetic acid, hydroxyethylidenediphosphonic acid, a sodium salt of either of these acids, or a mixture of two or more thereof. A sodium salt of ethylenediaminetetraacetic acid that may be ethylenediaminetetraacetic acid, tetrasodium salt, tetrahydrate. A commercially available ethylenediaminetetraacetic acid, tetrasodium salt, tetrahydrate that may be used may be available from Akzo Nobel under the trade designation Dissolvine 220-S. Dissolvine 220-S is identified by Akzo Nobel as being a chelating agent containing 83-85% by weight ethylenediaminetetraacetic acid, tetrasodium salt, tetrahydrate. The concentration of the chelator in the liquid sterilant composition may be in the range up to about 50% by weight, or from about 0.01% by weight to about 50% by weight, or from about 0.1% by weight to about 30% by weight.

The inventive process may comprise contacting articles contaminated with spores with the liquid sterilant composition for a sufficient period of time to effect a desired level of reduction (e.g., at least a 4 log reduction, or at least a 5 log reduction, or at least a 6 log reduction) in the number of spores capable of returning to vegetative growth, or in an embodiment, capable of reproduction, metabolism and/or growth. The articles that may be sterilized may include medical, dental, pharmaceutical, veterinary or mortuary instruments or devices (e.g., endoscopes), and the like. These may be made of a material comprising brass, copper, aluminum, stainless steel, carbon steel, plastic, glass, adhesive, or a combination of two or more thereof. The pH of the liquid sterilant may be in the range from about 2 to about 11, or from about 5.5 to about 7. The temperature of the liquid sterilant, when used in a sterilizing process, may be in the range from about 20 to about 80° C., or from about 40 to about 60° C. The exposure time of the article being sterilized to the liquid sterilant may be in the range from about 0.5 to about 240 minutes, or from about 2 to about 60 minutes.

The spores that may be treated (i.e., killed) include bacterial spores. The spores may comprise bacteria of the *Bacillus* or *Clostridia* genera. The spores may comprise *Geobacillus stearothermophilus*, *Bacillus atrophaeus*, *Bacillus subtilis*, *Bacillus pumilus*, *Bacillus coagulans*, *Clostridium sporogenes*, *Bacillus subtilis globigii*, *Bacillus cereus*, *Bacillus circulans*, *Bacillus anthracis*, or a mixture of two or more thereof. The spores may comprise one or more *Bacillus subtilis* strains and/or wild type *Bacillus subtilis* spores.

Figure 2:
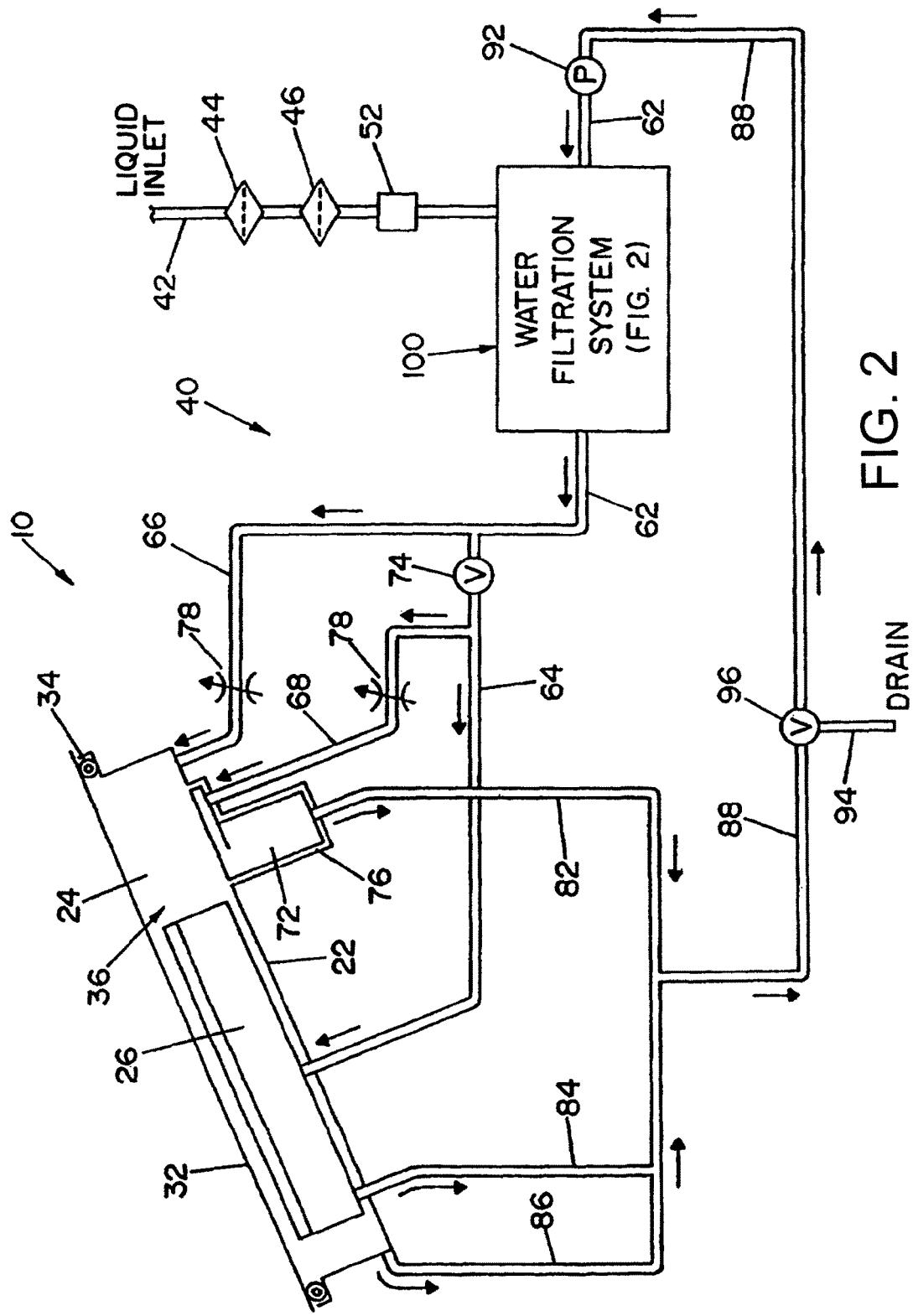
FIG. 2 is a flow sheet showing a decontamination or sterilization process that may be used in accordance with the invention.
Figure 3:
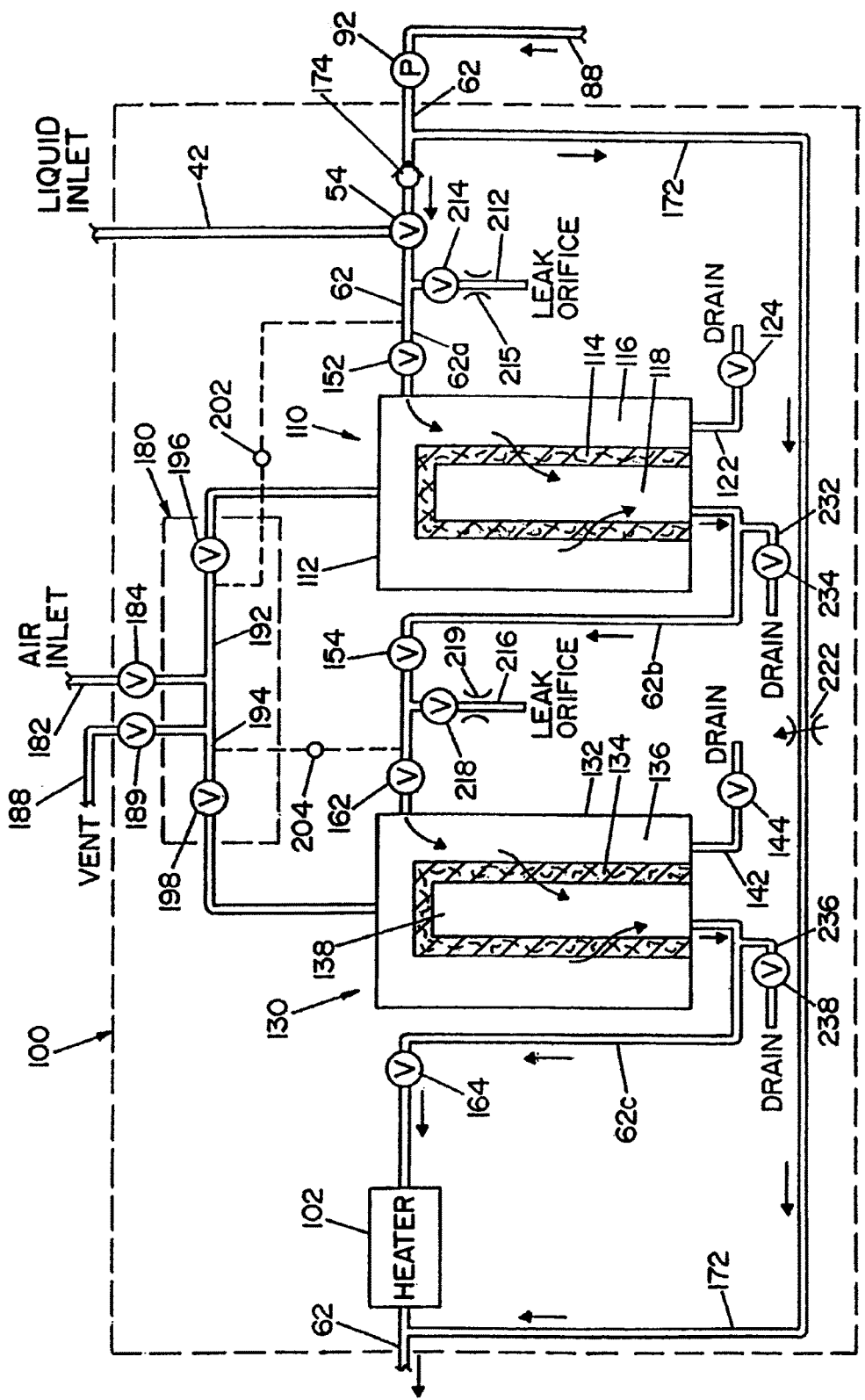
FIG. 3 is a flow sheet showing a filtration system that may be used with the sterilization process illustrated in FIG. 2.

The process may be conducted in any suitable decontamination or sterilization apparatus. An example of such sterilization apparatus is illustrated in FIGS. 2 and 3. Referring to FIGS. 2 and 3, sterilization apparatus 10 includes panel 22, which is part of a housing structure (not shown). The panel 22 includes a recess or cavity 24 dimensioned to receive the articles to be decontaminated or sterilized. A tray or container 26 is provided to receive the articles to be decontaminated or sterilized. Container 26 is dimensioned to be received within the recess or cavity 24.

A manually operable lid 32 is movable between an opened position allowing access to cavity 24, and a closed position (shown in FIG. 1) closing or covering cavity 24. A seal element 34 surrounds cavity 24 and forms a fluid-tight, i.e., an air-tight and liquid-tight, seal between lid 32 and panel 22 when lid 32 is in a closed position. A latch (not shown) is provided for latching and securing lid 32 in a closed position during a sterilization cycle. Cavity 24 defines sterilization chamber 36 when lid 32 is in the closed position.

A fluid circulation system 40 provides for the flow of the liquid sterilant to sterilization chamber 36 and for the circulation of the liquid sterilant in sterilization chamber 36. Fluid circulation system 40 may include a water inlet line 42 that is connected to a source of heated water (not shown). Filter elements 44 and 46 may be positioned in water inlet line 42 to filter out large contaminants that may be present in the incoming water. Filters 44 and 46 may comprise size exclusion filter elements used to remove particles exceeding a predetermined size. Filter element 46 may be used to filter out smaller particles than filter element 44. Filter element 44 may be used to filter out particles of about 3 micrometers or larger, and filter element 46 may be used to filter out particles of about 0.1 micrometer or larger. Pressure sensors (not shown) may be provided to monitor pressure drops across filter elements 44 and 46. A change in the pressure drop across either filter element may be indicative of clogging, rupturing or the like.

A viral reduction device 52 for inactivating organisms within the water source may be provided in water inlet line 42. Viral reduction device 52 may comprise an ultraviolet (UV) treatment device, for example, a class A device, as specified in NSF/ANSI Standards 55, or an equivalent thereof. An example of such a device would be a UV light system having a minimum dosage of 40,000 µW/cm2 which may be available from Wedeco Ideal Horizons of Charlotte, N.C. The viral reduction device 52 may be positioned downstream from filter elements 44 and 46, as shown in FIG. 2. Alternatively, the viral reduction device 52 may be positioned in water inlet line 42 upstream of the filter elements 44 and 46.

Water valve 54 may be used to control the flow of water from water inlet line 42 to system feeder line 62. System feeder line 62 includes filtration system 100 to filter out microscopic organisms and particles from the incoming water and thereby provide a sterile water supply to the fluid circulation system 40. System feeder line 62 splits into a first branch feeder line 64 and a second branch feeder line 66. First branch feeder line 64 is connected to container 26 within chamber 36. Second branch feeder line 66 is connected to chamber 36. Secondary branch feeder line 68 splits off of first branch feeder line 64 and is connected to the inlet portion of chemical delivery dispensing container 72. Dispensing container 72 contains the liquid sterilant ingredients used in the sterilization chamber 36. The container 72 may contain a concentrate containing the liquid sterilant ingredients with a reduced level of water where upon being mixed with water downstream of the container 72 the water concentrations indicated above for the sterilant are provided. Valve 74 controls the flow through first branch feeder line 64 and through secondary branch feeder line 68. Dispensing container is positioned within well 76 which is formed within panel 22. Flow restrictors 78 in second branch feeder line 66 and secondary branch feeder line 68 regulate fluid flow through these lines.

Branch return line 82 extends from chemical dispensing container 72 and is connected to system return line 88. Likewise, branch fluid return lines 84 and 86 extend from container 26 and chamber 36, respectively, and are connected to system return line 88. System return line 88 connects back with water inlet line 42 and fluid feeder line 62. Pump 92 is positioned in the system return line 88 and is used to circulate fluid through the fluid circulation system 40. Drain line 94 is connected to system return line 88. Drain valve 96 controls fluid flow to drain line 94.

Referring to FIG. 3, water filtration system 100 is positioned within fluid feeder line 62 and includes filter elements 114 and 134, shown as part of filter assemblies 110 and 130, respectively. First filter assembly 110 includes housing 112 and filter element 114. Second filter assembly 130 includes housing 132 and filter element 134. Filter elements 114 and 134 are positioned in series in fluid feeder line 62. A first section 62a of fluid feeder line 62 connects water inlet line 42 to the inlet side of first filter assembly 110. A second section 62b of fluid feeder line 62 connects the outlet side of first filter assembly 110 to the inlet side of second filter assembly 130. A third section 62c of fluid feeder line 62 connects the outlet side of second filter assembly 130 to heater 102.

Filter elements 114 and 134 may be bacterial retentive size exclusion filters. These may be used to filter out mycobacterium particles having particle sizes that are nominally about 0.12 µm or greater. Filter elements 114 and 134 may include a cylindrical support layer (not shown) made of material such as a polypropylene, surrounded by a filter membrane, such as a hydrophilic polyvinylidene difluoride (PVDF) or a polyethersulfone (PES) filter membrane. The filter membrane may be in the form of a capillary tube or hollow fiber member (or "fiber"), or in the form of a tubular sheath of a film formed either on the inner or outer surface of a tubular macroporous support, or a laminate sheet or film, or a laminate film deposited on the porous support. Suitable filter elements may be obtained from PTI Technologies of Oxnard, Calif.

Filter element 114 includes an annular outer chamber 116 and inner chamber 118. Outer chamber 116 comprises the upstream, pre-filtration side of filter element 114, and inner chamber 118 represents the downstream, filtered side of filter element 114. First section 62a of fluid feeder line 62 communicates with outer chamber 116, and second section 62b of feeder line 62 communicates with inner chamber 118. A drain line 122 communicates with outer chamber 116. Valve 124 is positioned in drain line 122 to regulate flow from the first filter assembly 110 to a drain.

Filter element 134 includes an annular outer chamber 136 and inner chamber 138. Outer chamber 136 comprises the upstream, pre-filtration side of filter element 134, and the inner chamber 138 represents the downstream, filtered side of filter element 134. Second section 62b of feeder line 62 communicates with outer chamber 136. Third section 62c of feeder line 62 communicates with inner chamber 138. Drain line 142 communicates with outer chamber 136 of second filter assembly 130. Valve 144 is positioned in drain line 142 to regulate flow from second filter assembly 130 to a drain.

The first and second filter assemblies 110 and 130 may be pre-sterilized prior to installation so that the contents of the filter assemblies 110 and 130 may be free of microbial contaminants. The filter assemblies 110 and 130 may be sterilized during each subsequent processing phase.

Valves 152 and 154 are positioned in fluid feeder line 62 to enable isolation of the first filter assembly 110. Valve 152 is positioned within first section 62a of fluid feeder line 62 at the inlet side of first filter assembly 110, and valve 154 is positioned in feeder line section 62b at the outlet side of first filter assembly 110. Similarly, valves 162 and 164 are positioned in fluid feeder line 62 to enable isolation of second filter assembly 130. Valve 162 is positioned in fluid line section 62b at the inlet side of second filter assembly 130, and valve 164 is positioned in fluid feeder line section 62c at the outlet side of second filter assembly 130.

A filter bypass line 172 is connected to fluid feed line 62 on opposite sides of the first and second filter assemblies 110 and 130. One end of bypass line 172 is connected to fluid feed line 62 between pump 92 and the location where the water inlet line 42 connects to fluid feed line 62. A directional check valve 174 is positioned between water inlet line 42 and filter bypass line 172 to prevent incoming water from entering filter bypass line 172. The other end of filter bypass line 172 is connected to feeder line 62 downstream of the filter assemblies 110 and 130, and the heater 102.

Filter purge manifold system 180, which includes air inlet line 182 and vent line 188, may be used to provide clean, filtered, pressurized air to the circulation system 40. Control valve 184 is positioned within air inlet line 182 to regulate the flow of air therethrough. The air in air inlet line 182 may be operated at a predetermined, regulated pressure. Air inlet line 182 may include a pressure regulator (not shown) for maintaining a generally constant, desired air pressure within air inlet line 182. Air inlet line 182 splits into two branch return lines 192 and 194. A vent line 188 with control valve 189 is connected to branch lines 192 and 194. Vent line 188 may be used to allow release of air from the water filtration system 100 during a fill cycle.

First branch line 192 extends through the housing 112 of first filter assembly 110 and communicates with outer chamber 116 of first filter assembly 110. Control valve 196 in first branch line 192 regulates the flow of air therethrough. Second branch line 194 extends through housing 132 of the second filter assembly 130 and communicates with outer chamber 136 of the second filter assembly 130. A control valve 198 is positioned within branch line 194 to regulate flow therethrough.

A first pressure sensor 202 is provided across the first section 62a of system feeder line 62 and branch line 192 to sense pressure on the upstream side of filter element 114.

A second pressure sensor 204 is provided across the second section 62b of system feeder line 62 and branch line 194 to sense pressure on the upstream side of filter element 134.

A first leak orifice line 212 is connected to first section 62a of fluid feed line 62 between the water inlet valve 54 and valve 152 on the upstream side of the first filter assembly 110. A valve 214 within leak orifice line 212 regulates flow therethrough. A flow restrictor 215 is positioned in leak orifice line 212 to regulate flow therethrough.

A second leak orifice line 216 is connected to second section 62b of fluid feed line 62 between valve 154 on the outlet side of first filter assembly 110 and valve 162 on the inlet side of second filter assembly 130. Valve 218 within leak orifice 216 regulates flow therethrough. A flow restrictor 219 is positioned in leak orifice line 216 to regulate flow therethrough.

A drain line 232 is connected to section 62b of system feeder line 62 on the downstream side of filter element 114. A valve 234 regulates flow therethrough. A drain line 236 is connected to section 62c of system feeder line 62 on the downstream side of filter element 134. A valve 238 regulates flow therethrough.

A system microprocessor (not shown) may be used to control the operation of circulation system 40 and the valves therein. The operation of circulation system 40 includes a water fill phase, a chemical generation and sterilization phase, a drain phase, one or more rinse phases, and a filter check phase.

Alternate embodiments of the water filtration system 100 that may be used are disclosed in U.S. Pat. No. 7,569,182 B2, at column 12, line 43 to column 13, line 46, and FIGS. 3 and 4, these passages and drawings being incorporated herein by reference.

A sterilization process may be conducted using the apparatus 10 as follows. One or more articles to be sterilized (e.g., medical, dental, pharmaceutical, veterinary or mortuary instruments or devices) are loaded into container 26, which in turn is placed into chamber 36. The articles may be supported on a tray, or in a basket, or a cartridge, or the like (not shown), within the container 26.

The articles may be decontaminated or sterilized using the liquid sterilant where ingredients of the liquid sterilant are placed in the dispensing device 72 and contacted with incoming water to form the liquid sterilant. At the beginning of a sterilization process, drain valve 96 in circulation system 40 is closed, and water valve 54 in inlet line 42 is opened to allow heated water to enter circulation system 40. The temperature of the water may be in the range from about 20 to about 80° C., or from about 40 to about 60° C. The incoming water is filtered using filter elements 44 and 46 in water inlet line 42 to remove particulates greater than a predetermined size. The water may be treated by using a viral reduction device 52 wherein ultraviolet (UV) radiation is applied to the water to inactivate organisms therein. The water passes through valve 54 and enters circulation system 40. The incoming water is filtered using filter assemblies 110 and 130 in feeder line 62 and proceeds to fill the circulation system 40, sterilization chamber 36 and container 26.

Check valve 174 between water inlet valve 54 and filter bypass line 172 causes all of the incoming water to flow through the first and second filter assemblies 110 and 130, thereby insuring filtration of the water flowing into apparatus 10.

The incoming water, which is under pressure from an external source, forces air in the fluid circulation system 40, sterilization chamber 36 and container 26 to an over-flow/air device (not shown) that may be positioned at the highest point of apparatus 10. Air within the system migrates toward the over-flow device.

The presence of the water flowing through the over-flow block is indicative that apparatus 10 is filled with water. The system controller then causes water valve 54 to close, thereby stopping the flow of water into apparatus 10, i.e., into fluid circulation system 40, sterilization chamber 36 and container 26. This completes the water fill phase of the process.

Once the apparatus 10 is filled with water, the system controller initiates the chemical mixing and exposure phase of the process. Pump 92 is energized to circulate water through circulation system 40, sterilization chamber 36 and container 26. Valve 74 is opened to initiate the flow of water through the dispensing container 72. The liquid sterilant flows into circulation system 40, wherein it is circulated through circulation system 40, sterilization chamber 36 and container 26 by pump 92. A portion of the liquid sterilant flows into sterilization chamber 36 around container 26, and a portion of the liquid sterilant flows into and through container 26 and contacts the articles contained therein.

As indicated by the arrows in FIG. 3, a portion of the circulated liquid sterilant flows through filter bypass line 172 and a portion of the liquid sterilant flows through feed line 62 and the filter assemblies 110 and 130. The amount of fluid flowing through the respective portions of the system may be controlled by regulating valve 222. The portion of the liquid sterilant flowing through filter feed line 62 and through the first and second filter assemblies 110 and 130 should be sufficient to insure sterilization of the filter elements 114 and 34 by exposure to the liquid sterilant. In this respect, the flow of the liquid sterilant through filter assemblies 110 and 130 sterilizes filter elements 114 and 134 and inactivates any microbial contamination that may have entered into filter assemblies 110 and 130 during the water fill phase. During each operation of apparatus 10, filter elements 114 and 134 may be exposed to liquid sterilant and as a result be sterilized by the sterilant. Moreover, the liquid sterilant that flows throughout the closed-loop, fluid circulation system 40 during a sterilization phase, effectively sterilizes the fluid circulation system 40, and the components and fluid conduits forming the same. In other words, fluid circulation system 40 is sterilized during each sterilization cycle.

After a predetermined exposure period, the drain phase may be initiated. The length of the exposure period may range from about 0.5 to about 240 minutes, or from about 2 to about 60 minutes. To initiate the drain phase, drain valve 96 is opened and the liquid sterilant is drained from the circulation system 40, sterilization chamber 36 and container 26.

After the liquid sterilant has been drained from the apparatus 10, one or more rinsing phases is performed to rinse any liquid sterilant and any residual matter from the sterilized articles. In this respect, inlet valve 54 is opened to introduce fresh water into apparatus 10, in a manner as heretofore described as the fill phase. All incoming water passes through the water filtration system 100, wherein water entering the circulation system 40 and sterilization chamber 36 is sterile. After each rinse fill, the rinse water is drained from apparatus 10 as heretofore described. Pump 92 may be activated to circulate the rinse water through apparatus 10. During each fill, circulation and drain phase, the fluid over-flow/air make-up assembly operates to prevent microbial contaminants from entering the internal environment within the system. The sterilized article may then be removed from the sterilization chamber.

EXAMPLES

The efficacy of the inventive process is assessed using a time kill suspension test method and spores of *Bacillus subtilis*.

Peracetic acid (PAA) and hydrogen peroxide ($H_2O_2$) are prepared as concentrated stocks (3× concentrate). Each test contains 100 µl of the PAA concentrate and 100 µl of the $H_2O_2$ concentrate. Controls containing only PAA or $H_2O_2$ are also prepared. These contain 100 µl of either the PAA concentrate or $H_2O_2$ concentrate and 100 µl of de-ionized water. To each test, 100 µl of spores are added while starting the timer concurrently. The samples are mixed thoroughly. The temperature of the samples is room temperature. At the appropriate contact times, 10 µl of the appropriate test sample are placed into 90 µl of the appropriate neutralizing solution, mixed thoroughly and incubated for at least 10 minutes. Ten fold serial dilutions are prepared through $10^{-6}$ and plated using the drop counting method. The plates are then incubated aerobically at 37° C. for 1-2 days. Following incubation, colony forming units (CFU) are counted using standard plate count techniques and converted to log 10 values for analysis.

The results are indicated in the tables below.

TABLE 1

Time (min) to achieve 4 log reduction for various PAA/$H_2O_2$ combinations
(calculated from curves fitted to time/kill data)

| $H_2O_2$ concentration (%) (% by weight) | | | | | | | |
|---|---|---|---|---|---|---|---|
| 6.40 | 48.64 | 15.68 | 7.2 | 7.36 | 3.67 | 2.14 | 1.36 |
| 3.20 | 97.28 | 15.68 | 13.12 | 8.24 | 3.92 | 2.28 | 1.68 |
| 1.60 | 168.96 | 28.16 | 24.32 | 14.08 | 4.64 | 3.52 | 1.82 |
| 0.80 | 343.04 | 33.7 | 32.96 | 19.36 | 7.6 | 3.96 | 1.9 |
| 0.40 | 639.34 | 92.16 | 69.12 | 43.52 | 14.08 | 6.4 | 2.08 |
| 0.20 | 1213.99 | 286.72 | 209.12 | 92.16 | 32 | 11.92 | 2.22 |

TABLE 1-continued

Time (min) to achieve 4 log reduction for various PAA/H₂O₂ combinations
(calculated from curves fitted to time/kill data)

| | | | | | | | |
|---|---|---|---|---|---|---|---|
| 0.10 | 2305.13 | — | — | 337.92 | 54.4 | 19.36 | 3.28 |
| 0.00 | — | 711625 | 67744.68 | 6449.101 | 613.9362 | 70.40 | 4.64 |
| | 0.00 | 0.005 | 0.01 | 0.02 | 0.04 | 0.08 | 0.16 |
| | PAA concentration (% by weight) | | | | | | |

TABLE 2

PAA kill time divided by PAA/H₂O₂ kill time from values in table 1 (i.e. Potentiation of PAA activity in the presence of H₂O₂)

| H₂O₂ concentration (% by weight) | | | | | | | |
|---|---|---|---|---|---|---|---|
| 6.40 | — | 45384.25 | 9408.98 | 876.24 | 167.29 | 32.90 | 3.41 |
| 3.20 | — | 45384.25 | 5163.47 | 782.66 | 156.62 | 30.88 | 2.76 |
| 1.60 | — | 25270.77 | 2785.55 | 458.03 | 132.31 | 20.00 | 2.55 |
| 0.80 | — | 21116.47 | 2055.36 | 333.11 | 80.78 | 17.78 | 2.44 |
| 0.40 | — | 7721.63 | 980.10 | 148.19 | 43.60 | 11.00 | 2.23 |
| 0.20 | — | 2481.95 | 323.95 | 69.98 | 19.19 | 5.91 | 2.09 |
| 0.10 | — | — | — | 19.08 | 11.29 | 3.64 | 1.41 |
| | 0.00 | 0.005 | 0.01 | 0.02 | 0.04 | 0.08 | 0.16 |
| | PAA concentration (% by weight) | | | | | | |

TABLE 3

H₂O₂ kill time divided by PAA/H₂O₂ kill time from values in table 1 (i.e. Potentiation of H₂O₂ activity in the presence of PAA)

| H₂O₂ concentration (% by weight) | | | | | | | |
|---|---|---|---|---|---|---|---|
| 6.40 | — | 3.10 | 6.76 | 6.61 | 13.25 | 22.73 | 35.76 |
| 3.20 | — | 6.20 | 7.41 | 11.81 | 24.82 | 42.67 | 57.90 |
| 1.60 | — | 6.00 | 6.95 | 12.00 | 36.41 | 48.00 | 92.84 |
| 0.80 | — | 10.18 | 10.41 | 17.72 | 45.14 | 86.63 | 180.55 |
| 0.40 | — | 6.94 | 9.25 | 14.69 | 45.41 | 99.90 | 307.38 |
| 0.20 | — | 4.23 | 5.81 | 13.17 | 37.94 | 101.84 | 546.84 |
| 0.10 | — | — | — | 6.82 | 42.37 | 119.07 | 702.78 |
| | 0.00 | 0.005 | 0.01 | 0.02 | 0.04 | 0.08 | 0.16 |
| | PAA concentration (% by weight) | | | | | | |

The values shown in Table 1 represent the time taken (minutes) to achieve a 4 log reduction in spore count in the presence of either PAA or H₂O₂ alone, or in combination with each other. For PAA concentrations 0.005, 0.01, 0.02 and 0.04% (in the absence of H₂O₂), the values shown are extrapolated based on the experimental data obtained for PAA concentrations 0.08, 0.16 and 0.32%. Similarly, for H₂O₂ concentrations 0.1, 0.2 and 0.4% (in the absence of PAA), the values shown are extrapolated from experimental data. All other values are generated from spore kill data.

Table 2 illustrates the potentiation of spore killing by PAA when in the presence of H₂O₂. At higher PAA concentrations (0.08 and 0.16% PAA) relatively little activity is gained by the addition of even very high concentrations of H₂O₂. For example, 0.16% PAA is only 3.41 times more active in the presence of 6.4% H₂O₂, as compared to the activity of 0.16% PAA alone.

However, as the concentration of PAA is reduced, the effect of adding H₂O₂ becomes more dramatic, with PAA spore killing activity being hundreds, thousands and even tens of thousands of times greater when in the presence of low concentrations of H₂O₂. For example, 0.02% PAA is 333.11 times more active in combination with 0.8% H₂O₂ than when used alone.

Table 3 illustrates the potentiation of spore killing by H₂O₂ when in the presence of PAA. The enhancement of the spore killing activity of H₂O₂ when in the presence of PAA is far less pronounced, with relative improvement in the spore killing activity of H₂O₂ in combination with all but the highest concentrations of PAA being no greater than about 100 times.

While the invention has been explained in relation to various embodiments, it is to be understood that modifications thereof may become apparent to those skilled in the art upon reading the specification. Therefore, it is to be understood that the scope of the invention specified herein is intended to include all modifications that may fall within the scope of the appended claims.

The invention claimed is:

1. A process for sterilizing an article contaminated with bacterial spores using a liquid sterilant, the liquid sterilant consisting essentially of water, peracetic acid, acetic acid, sulfuric acid and hydrogen peroxide, the article comprising a medical, dental, pharmaceutical, veterinary or mortuary instrument, the liquid sterilant having a concentration of the hydrogen peroxide in the range from 0.1 to 0.8% by weight, the concentration of the peracetic acid being in the range from about 0.005 to 0.08% by weight, the weight ratio of the peracetic acid to the hydrogen peroxide being in the range from 0.001 to about 0.1, the concentration of acetic acid being in the range from 0.001 to 0.3% by weight, the concentration of sulfuric acid being in the range from 0.001 to 0.3% by weight; wherein the process is conducted using a sterilizing apparatus which comprises a sterilization chamber and a sterilant introduction system, the process comprising:

placing the contaminated article in the sterilization chamber;

flowing the liquid sterilant from the sterilant introduction system into the sterilization chamber in contact with the contaminated article, maintaining the liquid sterilant at a temperature in the range from about 20° C. to about 80° C. in contact with the contaminated article for a period of time in the range from about 0.5 to about 240 minutes to sterilize the article and effect at least a 4 log reduction in the number of bacterial spores that are capable of returning to vegetative growth;

draining the liquid sterilant from the sterilization chamber;

flowing rinse water in the sterilization chamber in contact with the article; and removing the article from the sterilization chamber.

2. The process of claim 1 wherein the article is made of a material comprising brass, copper, aluminum, stainless steel, carbon steel, plastic, glass, adhesive or a combination of two or more thereof.

3. The process of claim 1 wherein the article comprises an endoscope.

4. The process of claim 1 wherein the temperature of the liquid sterilant is in the range from about 40° C. to about 60° C.

5. The process of claim 1 wherein the contact time of the article with the liquid sterilant is in the range from about 2 to about 60 minutes.

6. The process of claim 1 wherein the water comprises tap water, deionized water, distilled water, water purified by osmosis, or a mixture of two or more thereof.

7. The process of claim 1 wherein the bacterial spores comprise bacteria of the *Bacillus* or *Clostridia* genera.

8. The process of claim 1 wherein the bacterial spores comprise *Geobacillus stearothermophilus* spores *Bacillus atrophaeus* spores, *Bacillus subtilis* spores, *Bacillus pumilus* spores, *Bacillus coagulans* spores, *Clostridium sporogenes* spores, *Bacillus subtilis* globigii spores, *Bacillus cereus* spores, *Bacillus circulans* spores, *Bacillus anthracis* spores, or a mixture of two or more thereof.

9. The process of claim 1 wherein the bacterial spores comprise one or more *Bacillus subtilis* strains.

* * * * *